United States Patent
Tsai et al.

(10) Patent No.: US 8,263,332 B2
(45) Date of Patent: Sep. 11, 2012

(54) MISMATCHED END DNA LIGASE

(75) Inventors: Chun Tsai, Stanford, CA (US); Seonhi Kim, Menlo Park, CA (US); Gilbert Chu, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 452 days.

(21) Appl. No.: 11/871,023

(22) Filed: Oct. 11, 2007

(65) Prior Publication Data

US 2008/0160526 A1    Jul. 3, 2008

Related U.S. Application Data

(60) Provisional application No. 60/851,594, filed on Oct. 12, 2006.

(51) Int. Cl.
| | |
|---|---|
| C12Q 1/68 | (2006.01) |
| C12P 1/00 | (2006.01) |
| C12P 19/00 | (2006.01) |
| C12P 19/26 | (2006.01) |
| C12P 19/28 | (2006.01) |
| C12P 19/30 | (2006.01) |
| C12P 19/34 | (2006.01) |

(52) U.S. Cl. ............. 435/6.1; 435/41; 435/72; 435/84; 435/85; 435/89; 435/91.1; 435/91.5; 435/91.52

(58) Field of Classification Search ............... None
See application file for complete search history.

(56) References Cited

PUBLICATIONS

Ahnesorg et al., "XLF interacts with the XRCC4-DNA ligase IV complex to promote DNA nonhomologous end-joining," Cell, 2006, 124(2):301-313.
Budman et al., "Processing of DNA for nonhomologous end-joining by cell-free extract," EMBO J, 2005, 24(4):849-860.
Callebaut, et al., "Cernunnos interacts with the XRCC4 x DNA-ligase IV complex and is homologous to the yeast nonhomologous end-joining factor Nej1," J Biol. Chem., 2006, 281(20):13857-13860.
Drouet et al., "Interplay between Ku, Artemis, and the DNA-dependent protein kinase catalytic subunit at DNA ends," J Biol. Chem., 2006, 281(38):27784-27793.
Hartley et al., "DNA-dependent protein kinase catalytic subunit: a relative of phosphatidylinositol 3-kinase and the ataxia telangiectasia gene product," Cell, 1995, 82(5):849-856.
Li et al., "The XRCC4 gene encodes a novel protein involved in DNA double-strand break repair and V(D)J recombination," Cell, 1995, 83(7):1079-1089.
Li et al., "Identification of the XRCC4 gene: complementation of the DSBR and V(D)J recombination defects of XR-1 cells," Curr. Top. Microbiol. Immunol., 217:143-150, (1996).
Ma et al., "A biochemically defined system for mammalian nonhomologous DNA end joining," Mol. Cell, 2004, 16(5):701-713.
Mimori et al., "Isolation and characterization of cDNA encoding the 80-kDa subunit protein of the human autoantigen Ku (p70/p80) recognized by autoantibodies from patients with scleroderma-polymyositis overlap syndrome," Proc. Natl. Acad. Sci. U S A, 1990, 87(5):1777-1781.
Reeves et al., "Molecular cloning of cDNA encoding the p70 (Ku) lupus autoantigen," J Biol. Chem., 1989, 264(9):5047-5052.
Wei et al., "Molecular cloning and expression of human cDNAs encoding a novel DNA ligase IV and DNA ligase III, an enzyme active in DNA repair and recombination," Mol. Cell. Biol., 1995, 15(6):3206-3216.

*Primary Examiner* — Young J Kim
(74) *Attorney, Agent, or Firm* — Bozicevic, Field & Francis LLP; Pamela J. Sherwood

(57) ABSTRACT

A mismatched end DNA ligase is provided, which ligates two single strands to each other at a high efficiency, even if the other two single strands are not compatible. In one embodiment, the polypeptides of the ligase are Ku, Cernunnos, and XRCC4/Ligase4 (XL). This association can ligate DNA ends with a 3' overhang to a recessed 5' end, to a blunt end, or to a compatible end. In another embodiment, the proteins are Ku, Cernunnos, XRCC4/Ligase4 (XL) and DNA-PK.

11 Claims, 8 Drawing Sheets

Fig. 2.
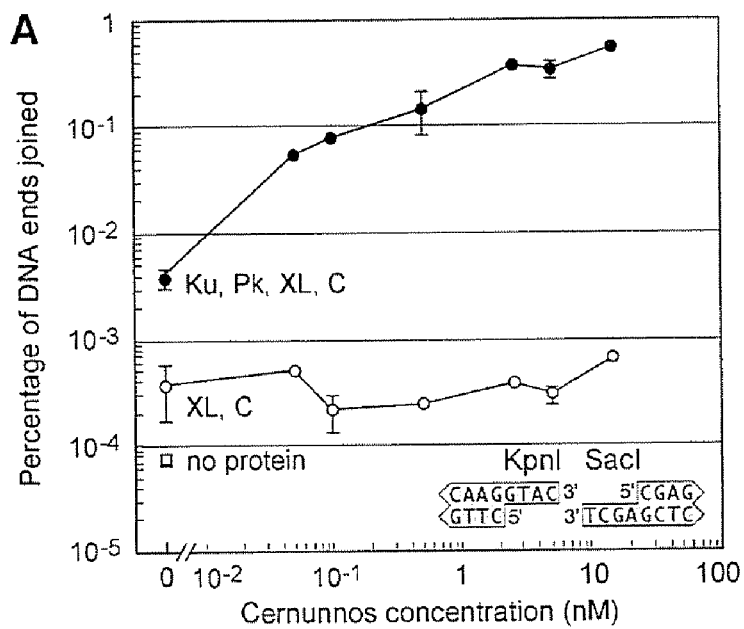
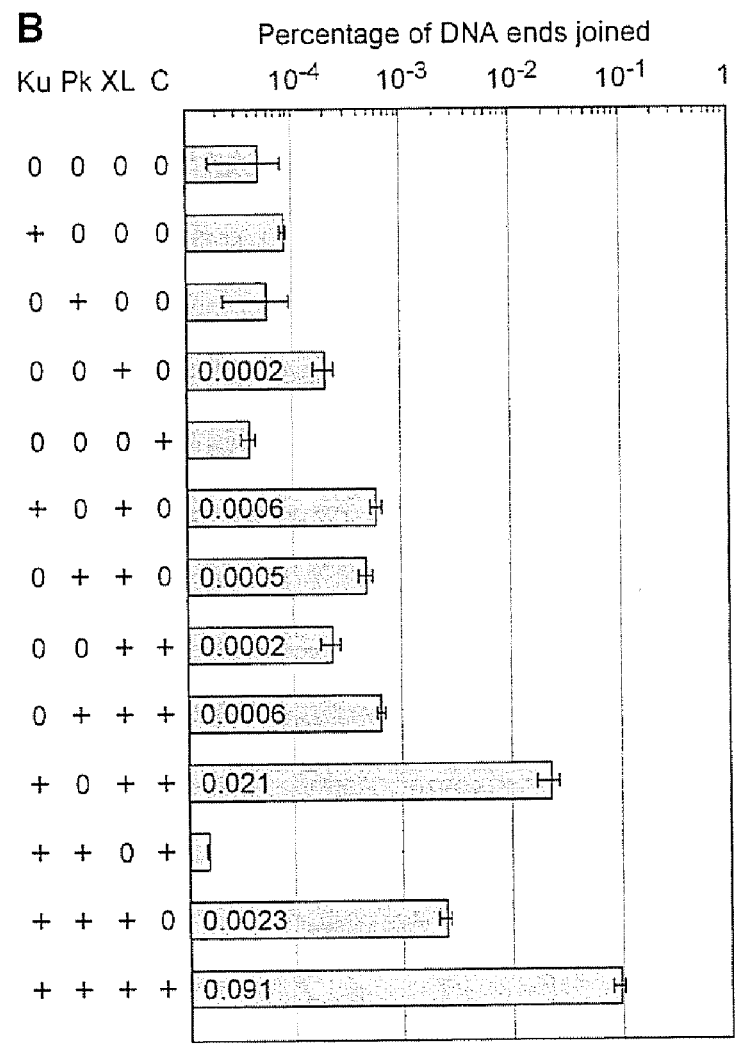

|  | Ku, Pk, XL<br>− Cernunnos | Ku, Pk, XL<br>+ Cernunnos | Ku, XL<br>− Cernunnos | Ku, XL<br>+ Cernunnos |
|---|---|---|---|---|

Input DNA ends ↓ % ends joined → Junctions

| EcoRV / BamHI | EcoRV / BamHI | EcoRV / BamHI | EcoRV / BamHI |
|---|---|---|---|
| ⟨CAAGGAT 3' 5'GATCCGAG⟩<br>⟨GTTCCTA 5'     3'GCTC⟩ | ⟨CAAGGAT 3' 5'GATCCGAG⟩<br>⟨GTTCCTA 5'     3'GCTC⟩ | ⟨CAAGGAT 3' 5'GATCCGAG⟩<br>⟨GTTCCTA 5'     3'GCTC⟩ | ⟨CAAGGAT 3' 5'GATCCGAG⟩<br>⟨GTTCCTA 5'     3'GCTC⟩ |
| ↓ 0.0014% | ↓ 0.012% | ↓ 0.0052% | ↓ 0.014% |
| ⟨CAAGGAT 3' 5'GATCCGAG⟩ 2<br>⟨GTTCCTA 5' 3'CTAGGCTC⟩ | ⟨CAAGGAT 3' 5'GATCCGAG⟩ 11<br>⟨GTTCCTA 5' 3'CTAGGCTC⟩ | ⟨CAAGGAT 3' 5'GATCCGAG⟩ 2<br>⟨GTTCCTA 5' 3'CTAGGCTC⟩ | ⟨CAAGGAT 3' 5'GATCCGAG⟩ 7<br>⟨GTTCCTA 5' 3'CTAGGCTC⟩ |
| ⟨CAAGGAT 3' 5'[   CGAG⟩ 1<br>⟨GTTCCTA 5' 3'    GCTC⟩ 9 | ⟨CAAGGAT 3' 5'[   CGAG⟩ 8<br>⟨GTTCCTA 5' 3'    GCTC⟩ | ⟨CAAGGAT 3' 5'[   CGAG⟩ 15<br>⟨GTTCCTA 5' 3'    GCTC⟩ | ⟨CAAGGAT 3' 5'[   CGAG⟩ 9<br>⟨GTTCCTA 5' 3'    GCTC⟩ |

| EcoRV / EcoRI | EcoRV / EcoRI | EcoRV / EcoRI | EcoRV / EcoRI |
|---|---|---|---|
| ⟨CAAGGAT 3' 5'AATTCGAG⟩<br>⟨GTTCCTA 5'     3'GCTC⟩ | ⟨CAAGGAT 3' 5'AATTCGAG⟩<br>⟨GTTCCTA 5'     3'GCTC⟩ | ⟨CAAGGAT 3' 5'AATTCGAG⟩<br>⟨GTTCCTA 5'     3'GCTC⟩ | ⟨CAAGGAT 3' 5'AATTCGAG⟩<br>⟨GTTCCTA 5'     3'GCTC⟩ |
| ↓ 0.0018% | ↓ 0.014% | ↓ 0.0022% | ↓ 0.018% |
| ⟨CAAGGAT 3' 5'AATTCGAG⟩ 3<br>⟨GTTCCTA 5' 3'TTAAGCTC⟩ | ⟨CAAGGAT 3' 5'AATTCGAG⟩ 5<br>⟨GTTCCTA 5' 3'TTAAGCTC⟩ | ⟨CAAGGAT 3' 5'[   CGAG⟩ 1<br>⟨GTTCCTA 5' 3'    GCTC⟩ 2 | ⟨CAAGGAT 3' 5'AATTCGAG⟩ 1<br>⟨GTTCCTA 5' 3'TTAAGCTC⟩ |
| ⟨CAAGGAT 3' 5'[   CGAG⟩ 13<br>⟨GTTCCTA 5' 3'    GCTC⟩ | ⟨CAAGGAT 3' 5'[   CGAG⟩ 1<br>⟨GTTCCTA 5' 3'    GCTC⟩ 4 |  | ⟨CAAGGAT 3' 5'[   CGAG⟩ 10<br>⟨GTTCCTA 5' 3'    GCTC⟩ |

MISMATCHED END DNA LIGASE

FEDERALLY-SPONSORED RESEARCH OR DEVELOPMENT

This invention was made with Government support under contract GM058120 awarded by the National Institutes of Health. The Government has certain rights in this invention.

BACKGROUND OF THE INVENTION

In molecular biology, ligases act to create a phosphodiester bond between strands of DNA or RNA. DNA ligase connects broken DNA strands to form covalent phosphodiester bonds between 3' hydroxyl ends of one nucleotide with the 5' phosphate end of another, using ATP in the process. The known DNA ligases in mammalian cells include DNA ligase I, which ligates Okazaki fragments during lagging strand DNA replication. DNA ligase III complexes with DNA repair protein XRCC1 to aid in sealing base excision mutations and recombinant fragments, and DNA ligase II is an alternatively spliced form of DNA ligase III. DNA ligase IV complexes with XRCC4 and catalyzes the final step in the non-homologous end joining DNA double-strand break repair pathway. It is also required for V(D)J recombination, the process which generates diversity in immunoglobulin and T-cell receptor loci during immune system development.

DNA ligases have become an indispensable tool in modern molecular biology research for generating recombinant DNA sequences. For example, DNA ligases are used with restriction enzymes to insert DNA fragments, often genes, into plasmids. Common commercially available DNA ligases were originally discovered in bacteriophage T4, *E. coli* or other bacteria. Using these enzymes, the most efficient way for a ligase to link DNA fragments is to connect two sticky ends together from a restriction digest. The hydrogen bonds between the complementary bases aid ligase in holding the two ends together while the phosphodiester bond is formed.

DNA double-strand breaks (DSBs) occur at random upon genotoxic stresses and represent obligatory intermediates during physiological DNA rearrangement events such as the V(D)J recombination in the immune system. DSBs, which are among the most toxic DNA lesions, are repaired by either homologous recombination or nonhomologous end joining (NHEJ), preferentially by the nonhomologous end-joining (NHEJ) pathway in higher eukaryotes. Failure to properly repair DSBs results in genetic instability, developmental delay, and various forms of immunodeficiency. Repair of DNA double strand breaks (DSB) by the nonhomologous end-joining pathway in mammals requires at least seven proteins involved in a simplified two-step process: (i) recognition and synapsis of the DNA ends dependent on the DNA-dependent protein kinase (DNA-PK) formed by the Ku70/Ku80 heterodimer and the catalytic subunit DNA-PKcs in association with Artemis; (ii) ligation dependent on the DNA ligase IV.XRCC4.Cernunnos-XLF complex (Drouet et al. (2006) J Biol Chem. 281(38):27784-93).

It has been reported that T4 DNA ligase, unlike *Escherichia coli* DNA ligase, Taq DNA ligase and Ampligase, is able to join the ends of single-stranded DNA in the absence of any duplex DNA structure at the ligation site. However, such nontemplated ligation of DNA oligomers catalyzed by T4 DNA ligase occurs with a very low yield, and thus is insignificant in many molecular biological applications of T4 DNA ligase.

DNA ligase enzymes are of commercial interest for catalysis of a variety reactions. The present invention provides a useful complex that acts as a single-strand DNA ligase.

SUMMARY OF THE INVENTION

The present invention relates to a mismatched end DNA ligase. Conventional ligases join both strands of two DNA ends. The ends must be compatible, consisting of either two blunt ends, or two ends with overhanging single strands that are complementary to each other. By contrast, the mismatched end DNA ligase of the invention will act on noncompatible DNA ends, ligating two single strands to each other even if the other two single strands are not compatible, thus the term "Mis-matched End (MEnd) DNA ligase".

In one embodiment, a purified polypeptide composition is provided, where multiple polypeptides coordinate to catalyze ligation of mismatched DNA strands at high efficiency. Such a group of polypeptides may be referred to as a complex or association, although the term does not, in this context, imply direct molecular interaction between the different polypeptides. In one such embodiment, the polypeptides are eukaryotic proteins, e.g. proteins from animals, including mammals.

In one such embodiment, the polypeptides of the association are Ku, Cernunnos, and XRCC4/Ligase4 (XL). This association can ligate DNA ends with a 3' overhang to a recessed 5' end, to a blunt end, or to a compatible end. The ligation efficiency of noncompatible ends is from around 10% of that seen for compatible ends. In another embodiment, the proteins are Ku, Cernunnos, XRCC4/Ligase4 (XL) and DNA-PK.

In another embodiment, the invention relates to an in vitro method of ligating nucleotides or nucleotide analogs or nucleic acids containing nucleotides or nucleotide analogs, comprising contacting polynucleotides or nucleic acids with polypeptides of the invention, wherein the ligase catalyzes a reaction of ligation of the nucleotides, nucleotide analogs or nucleic acids. The polynucleotides used in the methods of the invention may be RNA or DNA, including single-stranded RNA or DNA. The nucleotide analogs may contain modified bases, modified sugars and/or modified phosphate groups.

In another embodiment, a method is provided to screen candidate agents, e.g. polypeptides and associations thereof, for mis-matched end DNA ligase activity. In such methods, a candidate agent is contacted with polynucleotides in a joining reaction. The polynucleotide substrate preferably has non-compatible ends. The efficiency of ligation may be assessed by various criteria, e.g. by PCR, using primers that amplify on ligated ends. The ability of a candidate agent to catalyze mis-matched end DNA ligation is evidenced by the ability to join mis-matched ends.

BRIEF DESCRIPTION OF THE DRAWINGS

The foregoing and other objects, features and advantages of the invention will be apparent from the following more particular description of preferred embodiments of the invention, as illustrated in the accompanying drawings.

FIGS. 2A-B. Ku, DNA-PKcs, XL and Cernunnos act in concert to join mismatched 3' overhangs. (A) Cernunnos stimulates joining of mismatched ends by Ku, DNA-PKcs and XL, but not by XL alone. DNA substrates with mismatched 3'-3' overhangs (KpnI-SacI) were incubated with XL alone or XL, Ku and DNA-PKcs (Pk). Concentrations of Ku, DNA-PKcs and XL were 5 nM, 5 nM and 0.5 nM, respectively. Cernunnos (C) was added at concentrations of: 0.05 nM, 0.1 nM, 0.5 nM, 2.5 nM, 5 nM and 15 nM. The point in the lower left shows the background PCR signal in the absence of protein. Error bars represent the variation in duplicate measurements. (B) Cernunnos requires Ku to promote mismatched end joining by XL. DNA substrates with mismatched 3' overhangs (KpnI-SacI) were incubated with different combinations of the core NHEJ proteins Ku, DNA-PKcs, XL and Cernunnos (2.5 nM).

FIG. 3. Cernunnos promotes retention of overhanging ends. We incubated DNA substrates with Ku, DNA-PKcs and XL, with or without the addition of Cernunnos. The DNA substrates had mismatched 3'-3' ends (KpnI-SacI); blunt-3' ends with 4 nucleotide overhangs (EcoRV-KpnI); or blunt-3' ends with 2 nucleotide overhangs (EcoRV-SacII). We used quantitative PCR to measure the percentage of DNA ends joined and sequenced products from each reaction to characterize the junctions. The legend at the top of the figure indicates how the data are presented for each reaction. The junctions recovered from PCR amplification are depicted to show nucleotide addition (black background) and nucleotide deletion (white background).

FIG. 7. Addition of Cernunnos weakly promotes retention of 5' overhangs. DNA substrates for joining were mismatched blunt-5' ends EcoRV-BamHI (Upper) or EcoRV-EcoRI (Lower). We tested the effect of adding Cernunnos to Ku, DNA-PKcs, and XL (Left) or to Ku and XL (Right). We observed increased retention of 5' overhangs for EcoRV-BamHI ends (P=0.0002), but not for EcoRV-EcoRI ends (P=0.47).

DETAILED DESCRIPTION OF THE EMBODIMENTS

Figure 1:
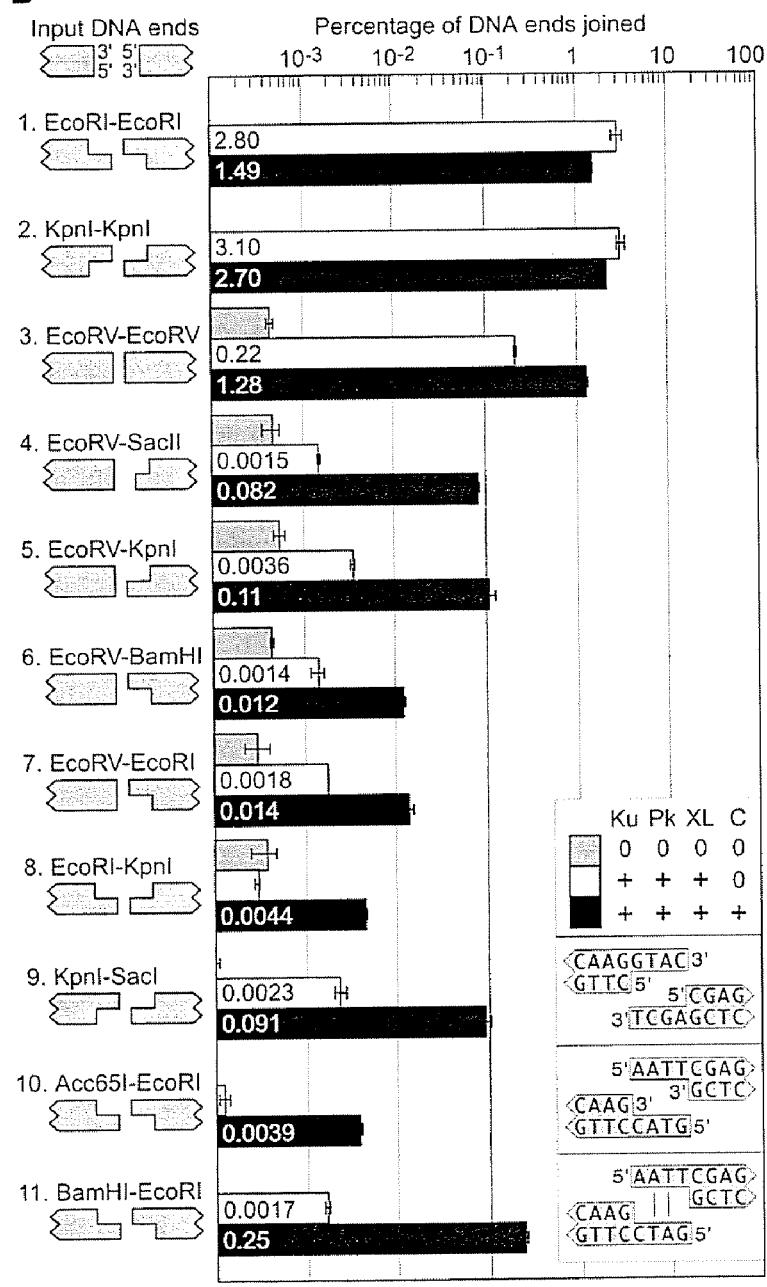
FIGS. 1A-B. Cernunnos stimulates joining of mismatched DNA ends. (A) Purification of NHEJ proteins. Commassie staining after SDS-PAGE shows our purified preparations of Ku, DNA-PKcs (Pk), Cernunnos (C), and XRCC4/Ligase IV (XL). (B) Cernunnos stimulates joining of non-cohesive ends by Ku, DNA-PKcs and XL. Linear DNA substrates were incubated with no protein (dark gray bars), Ku, DNA-PKcs and XL (light gray bars), or Ku, DNA-PKcs, XL and Cernunnos (black bars). The orientation of DNA is depicted in the upper left corner. We tested compatible ends (rows 1-3) with cohesive 5' overhangs (EcoRI-EcoRI), cohesive 3' overhangs (KpnI-KpnI), or blunt ends (EcoRV-EcoRV). We also tested 8 combinations of mismatched ends (rows 4-11). Note that SacII creates a 2 nucleotide 3' overhang. All other 3' and 5' overhangs were 4 nucleotides. The lower right panels show the overhangs from the KpnI-SacI, Acc65I-EcoRI and EcoRI-BamHI ends. We measured joining efficiency by quantitative PCR and expressed efficiency as percentage of input DNA ends joined. Because of differences among experiments, we plotted joining efficiency on a logarithmic scale. Concentrations of Ku, DNA-PKcs, XL and Cernunnos were 5 nM, 5 nM, 0.5 nM and 2.5 nM respectively, in this figure and in all other figures unless otherwise noted.

Polypeptides are provided that provides for efficient ligation of noncompatible DNA ends. An association of polypeptides is shown herein to provide for ligase activity that will act on noncompatible DNA ends. In one embodiment, purified polypeptides are provided, where the association of the polypeptides in a reaction mixture catalyzes ligation of DNA single strands at high efficiency. The polypeptides may include Ku, Cernunnos, and XRCC4/Ligase4 (XL) and optionally DNA-PK.

In another embodiment, the invention relates to a method of ligating nucleotides or nucleotide analogs or nucleic acids containing nucleotides or nucleotide analogs, comprising contacting polynucleotides or nucleic acids with the polypeptides of the invention, wherein the ligase catalyzes a ligation reaction of the nucleotides, nucleotide analogs or nucleic acids. The polynucleotides used in the methods of the invention may be RNA or DNA, including single-stranded RNA or DNA. The nucleotide analogs may contain modified bases, modified sugars and/or modified phosphate groups.

Reactions of interest are performed in vitro, and join polynucleotides that have noncompatible ends, i.e. the terminus of one polynucleotide does not base pair with the terminus of the polynucleotide to be joined. Reactions of interest include reactions where a blunt terminus is joined to a blunt terminus; where a blunt terminus is joined to a 5' overhang, where a blunt terminus is joined to a 3' overhang, where two 5' overhangs are joined, where two 3' overhangs are joined, or where single stranded molecules are joined. In general at least one terminus will comprise a 5' phosphate group. Where 3' overhangs are ligated, the sequence of one of the overhangs is maintained. By the term 5' overhang, or 3' overhang, reference is made to a double stranded polynucleotide where the terminus comprises a single stranded region of at least one nucleotide, which may comprise 2, 3, 4, 5, or more nucleotides in a single stranded conformation, where the terminal nucleotide may be in a 3' orientation or a 5' orientation. A blunt terminus comprises no single stranded regions.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Methods recited herein may be carried out in any order of the recited events which is logically possible, as well as the recited order of events.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Single-strand DNA ligase activity permits construction of recombinant DNA molecules without the usual limitation of compatible ends imposed by conventional ligases. Methods of use for the MEnd DNA ligase include, without limitation:

Cloning of PCR-amplified DNA. During PCR amplification of DNA, Taq polymerase often catalyzes the non-templated addition of one or two bases, creating a 3' overhang. Thus, PCR products are not blunt-ended and cloning efficiency is compromised by the need to use specialized cloning vectors. The MEnd single-strand DNA ligase will permit these fragments to be ligated directly into a blunt-ended cloning vector.

Random cloning of genomic DNA. Current technologies for fragmenting genomic DNA leave ends with protruding single strands. If DNA polymerase is used to convert protruding 5' overhangs into blunt ends, the genomic DNA fragments will have blunt ends and protruding 3' overhangs. The MEnd single-strand DNA ligase will ligate these fragments directly onto a cloning vector.

Cloning of full-length cDNA. Currently, there is no reliable method for cloning full-length cDNA from mRNA. Second strand DNA synthesis requires priming for polymerization that fails to copy sequences at the 3' end of the cDNA. Single-strand DNA ligase activity overcomes this difficulty. Using random hexamers as primers for second strand synthesis, single-strand DNA ligase will ligate the protruding 3' overhang directly into a cloning vector.

The MEnd DNA ligase of the invention is comprised of an association of polypeptides. The association is not required to be pre-assembled, it is sufficient to add the individual polypeptides in a reaction mixture, e.g. in the presence of polynucleotides to be ligated. In a preferred embodiment, one or more, or all of the polypeptides are purified prior to addition into a reaction mixture.

In some embodiments of the invention, a kit is provided for ligation, where the kit comprises at least the polypeptides Ku, Cernunnos, and XRCC4/Ligase4 (XL) and optionally comprises DNA-PK. One, two, three or all the polypeptides may be provided in a purified form. The polypeptides may be derived from any source, e.g. bacterial eukaryotic, etc. In some embodiments the polypeptides are derived from an animal source, e.g. from a mammalian source. The kit may further comprise a positive control mixture of nucleotides for ligation. The kit may further comprise buffer suitable for the reaction, for example provided as a concentrate, i.e. 10×, 100×, and the like.

The enzymes of the invention may be "isolated"; as used herein, an "isolated" polypeptide has been completely or partially purified from other polypeptides. For example, an isolated polypeptide of the invention may be substantially isolated with respect to the complex cellular milieu in which it naturally occurs. In some instances, the isolated material will form part of a composition (for example, a crude extract containing other substances), buffer system or reagent mix. In other circumstance, the polypeptide may be purified to essential homogeneity, for example as determined by PAGE or column chromatography such as HPLC. Thus, an isolated polypeptide can include a polypeptide that is synthesized chemically or by recombinant means.

The present invention also pertains to polypeptide sequences that are not necessarily found in nature but that have substantially similar activity to the polypeptides described below. The invention also encompasses variations of the polypeptide sequences of the molecules providing for DNA ligase activity, such as those encoding active fragments or active derivatives of the polypeptides. Such variations can be naturally-occurring, or non-naturally-occurring, such as those induced by various mutagens and mutagenic processes. Intended variations include, but are not limited to, addition, deletion and substitution of one or more amino acids that result in conservative or non-conservative amino acid changes, including additions and deletions; however, such alterations should preserve at least one activity of the polypeptide, i.e., the altered or mutant polypeptide should be an active derivative of the naturally-occurring polypeptide. For example, the mutation(s) can preferably preserve the three dimensional configuration of the binding site of the native polypeptide, or can preferably preserve the activity of the polypeptide (e.g., if the polypeptide is a DNA ligase, any mutations preferably preserve the ability of the enzyme to catalyze ligation of two polynucleotide strands). The presence or absence of activity or activities of the polypeptide can be determined by various standard functional assays including, but not limited to, assays for binding activity or enzymatic activity.

The methods of the invention may utilize polypeptide sequences that have a substantial identity with the polypeptide sequences of known Ku, Cernunnos, XRCC4/Ligase4 (XL) and DNA-PK sequences, for example having at least about 10%, preferably at least about 20%, more preferably at least about 30%, more preferably at least about 40%, even more preferably at least about 50%, yet more preferably at least about 70%, still more preferably at least about 80%, and even more preferably at least about 90% identity, and still more preferably 95% identity, and providing for a molecule having at least about 10%, preferably at least about 20%, more preferably at least about 30%, more preferably at least about 40%, even more preferably at least about 50%, yet more preferably at least about 70%, still more preferably at least about 80%, and even more preferably at least about 90% of the activity of the molecules exemplified herein. Variant and derivative sequences may include substantial regions of sequence identity, e.g. of at least about 50 contiguous amino acids identity, at least about 100 contiguous amino acids identity, at least about 150 contiguous amino acids identity, at least about 200 contiguous amino acids identity. Fragments may comprise at least about 50 contiguous amino acids, at least about 100 contiguous amino acids, at least about 150 contiguous amino acids, at least about 200 contiguous amino acids or more. An "active fragment," as referred to herein, is a portion of polypeptide (or a portion of an active derivative) that retains the polypeptide's activity, as described above.

Appropriate amino acid alterations can be made on the basis of several criteria, including hydrophobicity, basic or acidic character, charge, polarity, size, the presence or absence of a functional group (e.g., —SH or a glycosylation site), and aromatic character. Assignment of various amino adds to similar groups based on the properties above will be readily apparent to the skilled artisan; further appropriate amino acid changes can also be found in Bowie et al. (1990), Science, 247:1306-1310 (1990). For example, conservative amino acid replacements can be those that take place within a family of amino acids that are related in their side chains. Genetically encoded amino acids are generally divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cystine, serine, threonine, tyrosine. Phenylalanine, tryptophan and tyrosine are sometimes classified jointly as aromatic amino acids. For example, it is reasonable to expect that an isolated replacement of a leucine with an isoleucine or valine, an aspartate with a glutamate, a threonine with a serine or a similar conservative replacement of an amino add with a structurally related amino acid will not have a major effect on activity or functionality.

The polypeptides of the invention can also be fusion polypeptides comprising all or a portion (e.g., an active fragment) of the native polypeptide amino acid sequence fused to an additional component, with optional linker sequences. Additional components, such as radioisotopes and antigenic tags, can be selected to assist in the isolation or purification of the polypeptide or to extend the half life of the polypeptide; for example, a hexahistidine tag would permit ready purification by nickel chromatography. The fusion protein can contain, e.g., a glutathione-S-transferase (GST), thioredoxin (TRX) or maltose binding protein (MBP) component to facilitate purification; kits for expression and purification of such fusion proteins are commercially available. The polypeptides of the invention can also be tagged with an epitope and subsequently purified using antibody specific to the epitope using art recognized methods.

Polypeptides described herein can be isolated from naturally-occurring sources (e.g., isolated from host cells). Alternatively, the polypeptides can be chemically synthesized or recombinantly produced. For example, PCR primers can be designed to amplify the ORFs from the start codon to stop codon. The primers can contain suitable restriction sites for an efficient cloning into a suitable expression vector. The PCR product can be digested with the appropriate restriction enzyme and ligated between the corresponding restriction sites in the vector (the same restriction sites, or restriction sites producing the same cohesive ends or blunt end restriction sites).

The polypeptides of the present invention can be isolated or purified (e.g., to homogeneity) from cell culture (e.g., from culture of host cells infected with expression vector(s)) by a variety of processes. These include, but are not limited to, anion or cation exchange chromatography, ethanol precipitation, affinity chromatography and high performance liquid chromatography (HPLC). The particular method used will depend upon the properties of the polypeptide; appropriate methods will be readily apparent to those skilled in the art. For example, with respect to protein or polypeptide identification, bands identified by gel analysis can be isolated and purified by HPLC, and the resulting purified protein can be sequenced. The protein can be isolated by conventional means of protein biochemistry and purification to obtain a substantially pure product, i.e., 80, 95 or 99% free of cell component contaminants, as described in Jacoby, Methods in Enzymology, Volume 104, Academic Press, New York (1984); Scopes, Protein Purification, Principles and Practice, 2nd Edition, Springer-Verlag, New York (1987); and Deutscher (ed.), Guide to Protein Purification, Methods in Enzymology, Vol. 182 (1990).

MEnd DNA ligase polypeptides, as described herein can be used in a similar manner as other DNA ligases. In a typical reaction, the polynucleotides to be ligated are combined in a reaction mixture in vitro in the presence of an appropriate buffer, as exemplified in the Examples, ATP, and the polypeptides of the invention. As described herein, it is not necessary for the enzymes to have compatible ends. The reaction mixture is incubated for a period of time sufficient to allow for the desired level of ligation, e.g. for about 10, 30, 60 minutes or more. The polynucleotide substrate may be present at a concentration of from around 0.01 µM to around 100 mM, depending on the specific reaction, where smaller fragments may be present at a high molarity than larger fragments. The reaction is typically incubated under physiological conditions, e.g. at about 10, 15, 20, 25, 30, 35-37 degrees C. Buffers, such as Tris, etc., and salts may be included in the reaction mix as is known in the art, e.g. including one or more of Na, Mg, and K at concentrations from around 0.1 to 500 mM, and generally including ATP at a concentration of at least about 0.01 mM, more usually at least about 0.1 mM.

The ligase component enzymes may be included in a reaction mixture as follows:
(A) Ku at a concentration of at least about 0.1 mM, at least about 1 mM, at least about 2.5 mM, or more, usually not more than about 50 mM.
(B) XRCC4/Ligase IV at a concentration of at least about 0.01 mM, at least about 0.1 mM, at least about 0.25 mM, or more, usually not more than about 50 mM.
(C) Cernunnos/XLF at a concentration of at least about 0.05 mM, at least about 0.1 mM, at least about 1 mM, or more, usually not more than about 50 mM.
(D) DNA-PKcs is optionally included at a concentration of at least about 0.1 mM, at least about 1 mM, at least about 2.5 mM, or more, usually not more than about 50 mM.

The stoichiometry of the reaction may be as follows. The ratio of Ku:XRCC4 may range from around about 10:1 to 1:20 to 50:1. The ratio of Ku:Cernunnos may range from around about 2:1 to 1:20 to 20:1. DNA-PKcs is optionally included, and may range from around about 1:1 to 1:20 to 20:1 with respect to Ku.

Substrates for ligation may have non-compatible, e.g. 3' over hang ends, may have compatible ends, blunt ends, or may be single stranded. Usually such substrates have non-compatible ends, and are at least about 10 nucleotides in length, at least about 20 nucleotides in length, at least about 30 nucleotides in length, at least about 100 nucleotides in length, or longer. At least one of the ends to be ligated comprises a 5' $PO_4$.

The efficiency of ligation for blunt ends is usually around about 50%, around about 75%, around about 90% of the efficiency for ligation of compatible ends in a comparable reaction, or more. For example, in reaction conditions where from about 1% to about 3% of compatible ends are ligated, at least about 0.5%, at least about 1%, or more of blunt ends are joined.

The efficiency of a blunt end to a 3' overhang, or a 5' overhang to a blunt end, is around about 5%, around about 7.5%, around about 10% of the efficiency for ligation of compatible ends, or more. For example, in reaction conditions where from about 1% to about 3% of compatible ends are ligated, at least about 0.05%, at least about 0.1%, or more of 3' overhang, or a 5' overhang to a blunt end are joined.

The efficiency of ligation for two 3' overhangs is around about 5%, around about 7.5% around about 10% of the efficiency for ligation of compatible ends, or more.

The efficiency of ligation for a 3' overhang to a 5' overhang is around about 0.1%, 0.2%, 0.5% of the efficiency for ligation of compatible ends, or more. For example, in reaction conditions where from about 1% to about 3% of compatible ends are ligated, at least about 0.001%, at least about 0.002%, or more of a 3' overhang to a 5' overhang are joined.

Polypeptides Involved in MEnd DNA Ligations Include:

Cernunnos/XLF. Cernunnos-XLF is a nonhomologous end-joining factor. The sequence of various homologs may be accessed at Genbank, e.g. human (CAI99410), cow (XP_586059), and dog Cernunnos-XLF (XP_848099), and homologs thereof may be identified in various organisms by methods of sequence comparison, as known in the art. See, for examples, Ahnesorg et al. (2006) Cell. January 27; 124:301-313; Buck et al. (2006) Cell. January 27; 124:287-299; Callebaut et al. (2006) J. Biol Chem. May 19; 281(20):13857-60, each herein specifically incorporated by reference.

XRCC4/Ligase4 (XL). The DNA Ligase IV complex, consisting of the catalytic subunit DNA Ligase IV (Wei et al. (1995) Mol Cell Biol. 15(6):3206-16) and its cofactor XRCC4 (Li et al. (1995) Cell. 83:1079-89, Li and Alt (1996) Curr Top Microbiol Immunol. 217:143-50, each herein specifically incorporated by reference), performs the ligation step of repair. DNA ligase IV is conserved in all eukaryotes, and is part of a family of ATP-dependent DNA ligases that are involved in DNA replication, recombination and repair. These DNA ligases have two common domains: a catalytic domain (CD) that contains several conserved nucleotide-binding motifs, and a conserved non-catalytic domain (NCD). In addition, DNA ligase IV has a long C-terminal extension comprising of two BRCT domains (after the C-terminal domain of a breast cancer susceptibility protein, BRCA1), which are phosphopeptide-binding modules found in many proteins that regulate DNA damage responses, such as BRCA1, MDC1 and BARD1. A short linker region that is required for the binding of the XRCC4 protein, which is important for ligase activity, connects the two BRCT domains. DNA ligase IV is a nuclear enzyme that joins the breaks in the phosphodiester backbone of DNA. The reaction mechanism involves the formation of a covalent enzyme-AMP intermediate from the cleavage of ATP to AMP and pyrophosphate. The adenylate group from AMP is then transferred to the 5'-phosphate of the nicked DNA molecule. Finally, the DNA ligase seals the gap by phosphodiester bond formation, via the displacement of the AMP residue with the 3'-hydroxyl group from the adjacent DNA strand.

Ku. The Ku heterodimer, consisting of Ku70 (see Reeves and Sthoeger (1989) J Biol Chem. 264(9):5047-52) and Ku860 (Mimori et al. (1990) Proc Natl Acad Sci U.S.A. 87(5):1777-81, each herein specifically incorporated by reference). The Ku complex functions as the DNA binding component of DNA-dependent protein kinase (DNA-PK). Ku binds directly to the termini of DSBs and has end-bridging activity. Ku forms a ring that encircles duplex DNA, cradling two full turns of the DNA molecule. By forming a bridge between the broken DNA ends, Ku acts to structurally support and align the DNA ends, to protect them from degradation, and to prevent promiscuous binding to unbroken DNA. Ku effectively aligns the DNA, while still allowing access of polymerases, nucleases and ligases to the broken DNA ends to promote end joining. Once Ku is in place, it recruits the catalytic subunit of DNA-PK, a large catalytic polypeptide of approximately 350 kD (p350), which becomes activated when it associates with DNA-bound Ku. DNA-PKcs is a serine/threonine kinase in the phosphoinositide 3-kinase (PI3K) family that is believed to be a signaling molecule in response to cellular stress. DNA-PKcs can phosphorylate several nuclear proteins in vitro, including DNA ligase IV and XRCC4.

DNA-PK. DNA-PKcs (Hartley et al. (1995) Cell. 82(5): 849-56, herein specifically incorporated by reference).

While this invention has been particularly shown and described with references to preferred embodiments thereof, it will be understood by those skilled in the art that various changes in form and details may be made therein without departing from the spirit and scope of the invention as defined by the appended claims.

EXPERIMENTAL

Example 1

It was discovered that the proteins, Ku, Cernunnos, and XRCC4/Ligase4 (XL) could ligate DNA ends with noncompatible 3' overhangs. The DNA junctions always contained sequences in which one of the 3' overhangs was preserved. Thus, the protein complex ligated a 3' overhang to a recessed 5' end, displaying a single-strand DNA ligase activity. Additional experiments demonstrated that the complex could ligate an end with a 3' overhang to a blunt end or ligate two compatible ends. The ligation of noncompatible ends was 10% to 15% of that seen for compatible ends. DNA-PK boosts joining efficiency about 6-fold, but is not required. Upon addition of DNA-PK, ligation of noncompatible ends approached the efficiency seen for compatible ends.

Example 2

Purification of Recombinant Ku70/86 Heterodimer

Purified recombinant Ku70/86 heterodimer was produced by co-infecting Sf9 insect cells with baculoviruses containing sequences encoding Ku70-His and Ku86. Infect with limiting amounts of Ku70 virus. Collect cells at about 48 hours post-infection and flash-freeze. Store at −80° C. For purification, lyse cells in lysis buffer of 50 mM Na.$PO_4$ pH 8.0, 500 mM NaCl, 0.5% Igepal, 10% glycerol, 10 mM B-mercaptoethanol, 1 mM phenylmethanesulfonyl fluoride, 2.7 mM benzamidine, EDTA-free protease inhibitor cocktail tablet [Roche]). Sonicate cells. Clarify lysate with centrifugation in SS-34 rotor at 15,500 rpm for 30 minutes. Collect supernatant. Incubate with Ni-NTA beads in 20 mM imidazole. Wash 3× with wash buffer: 50 mM Na.$PO_4$ pH 7.4, 500 mM NaCl, 40 mM imidazoles, 0.5% Igepal, 10% glycerol, 10 mM B-ME). Elute with: 50 mM Na.$PO_4$ pH 7.4, 500 mM NaCl, 300 mM imidaole, 10% glycerol, 10 mM B-mercaptoethanol. Purify over Superose-12 gel filtration column. Elute with: 50 mM Na.$PO_4$ pH 7.4, 300 mM NaCl, 1 mM EDTA, 10% glycerol, 10 mM B-ME. Flash-freeze proteins and store at −80° C.

Example 3

Purification of Endogenous DNA-PKcs from HeLa Cells

Endogenous DNA-PKcs was purified by coupling Ku80C-derived peptide (KGSGEEGGDVDDLLDMI) (SEQ ID NO:1) to 1-ml NHS-activated HiTrap column (GE Healthcare). Dissolve 20 mg of the peptide in 1 ml of coupling buffer. Wash 1 ml of NHS-activated HiTrap resin with coupling buffer. Pour, into column and incubate with peptide overnight 4° C. Inject 6 ml of solution A. Inject 6 ml of solution B. Inject 6 ml of solution A. Leave the column overnight at +4° C. Inject 6 ml of solution B. Inject 6 ml of solution A. Inject 6 ml of solution B. Inject 2 ml of storage buffer. Coupling Buffer: 0.2 M NaHCO3 pH=8.3, 0.5 M NaCl; Solution A: 0.5 M 2-aminoethanol, 0.5 M NaCl, pH=8.3; Solution B: 0.5 M NaCl, pH=4; Storage Buffer: 0.05 M $Na_2HPO_4$, 0.1% $NaN_3$, pH=7.

Prepare nuclear extracts from 10 L HeLa cells (ordered from National Cell Culture Center). Thaw cells. Resuspend in 4 packed cell volumes of hypotonic lysis buffer: 10 mM KCl, 10 mM Tris-HCl, pH 7.9, 1 mM DTT, Protease Inhibitors. Incubate for 10 minutes on ice. Lyse by Dounce homogenization (Type B pestle). Collect cell nuclei by centrifugation (3,300×g) for 15 min. (SS-34: 5300 rpm). Wash pellet in same buffer as above. Centrifuge 3,300×g for 15 min. Resuspend pellet in 4 packed cell volumes of high salt buffer: 50 mM Tris-HCl, pH 7.9, 0.42 M KCl, 5 mM $MgCl_2$, 0.1 mM EDTA, 20% glycerol, 10% sucrose, 2 mM DTT, Protease inhibitors (5.7 ml 70% sucrose+34.3 ml buffer+80 ul 1M DTT+P/B). Stir nuclei for 30 minutes on ice. Centrifuge for 30 minutes at 26,500×g. Collect supernatant. (Ti-70: 19,000 rpm). Precipitate proteins by adding 0.33 g/ml $(NH_4)_2SO_4$. Centrifuge for 10 minutes at 20,500×g. (Ti-70: 16,700) Collect pellet. Resuspend pellet in buffer (1.5 ml/L original cell culture): 50 mM Tris-HCl, pH 7.9, 0.1 M KCl, 12.5 mM $MgCl_2$, 1 mM EDTA, 20% glycerol, 1 mM DTT, Protease inhibitors. Dialyze sample overnight against same buffer. (~50 volumes). Centrifuge for 10 minutes at 9,000×g. Collect supernatant.

Run NHS-activated HiTrap chromatography. Mix the extract with equal volume of 0.2 M NaCl chromatography buffer A. The final salt concentration should now be approx. 150 mM. Incubate extract with Ku80C-conjugated NHS-activated resin. Tumble overnight at 4° C. Spin the column material down at 2000 rpm, 3 min. Prepare 1 ml Pharmacia column for the chromatography on AKTA FPLC. Chromatography program: 0.05 ml/min, 10 ml 5% (50) mM buffer B, linear gradient from 5% to 100% buffer B in 6 ml, 6 ml at 100% buffer B, 10 ml at 5% buffer B, collect 200 μl fractions. Chromatography Buffer A: 25 mM HEPES-KOH, pH=7.5, 0.1 mM EDTA, 10% glycerol, 15% maltose, 10 mM B-mercaptoethanol Chromatography Buffer B: 25 mM HEPES-KOH, pH=7.5, 1 M NaCl, 0.1 mM EDTA, 10% glycerol, 15% maltose, 10 mM B-mercaptoethanol Purify DNA-PKcs over Superose-6 Gel Filtration Column. Pool less pure fractions and inject into column. Elute in: 50 mM Na.$PO_4$ pH 7.5, 5 mM EDTA, 100 mM NaCl, 10% glycerol, 20 mM B-mercaptoethanol.

Purify DNA-PKcs over Mono Q anion-exchange column. If skipping previous step, dialyze protein into: 50 mM Na.$PO_4$ pH 7.5, 5 mM EDTA, 100 mM NaCl, 10% glycerol, 20 mM B-MEA. Inject protein onto column. Elute with NaCl gradient: 50 mM Na.$PO_4$ pH 7.8, 5 mM EDTA, 10% glycerol, 20 mM B-mercapethanol, 50 mM NaCl to 1 M NaCl. Snap-freeze proteins and store at −80° C.

Example 4

Purification of Xrcc4/Ligase IV Complex

Co-infect insect Sf9 cells with baculoviruses containing XRCC4 and LigaseIV-His. Use limiting amounts LigaseIV-His virus. Harvest cells by centrifugation about 50 hours post-infection Flash-freeze and store −80° C. Lyse cells in lysis buffer: 20 mM Na.$PO_4$ pH 7.4, 0.5 M NaCl, 10 mM imidazoles, 1% IGEPAL-CA630, 5 mM β-mercaptoethanol, 1 mM phenylmethanesulfonyl fluoride, 2.7 mM benzamidine, EDTA-free protease inhibitor cocktail tablet [Roche]).

Sonicate cells. Clear lysate by centrifugation at 100,000×g for 1 h in TI-70 rotor. Mix supernatant with Ni-NTA-agarose beads (Qiagen) in the presence of 20 mM imidazole for 1 h at 4° C. Pack beads into a column and wash several times with wash buffer with alternating pHs of 7.4 and 6.0. 20 mM $NaH_2PO_4$, 0.5 M NaCl, 20 mM imidazoles, 5 mM β-ME, 10% glycerol. Elute proteins with wash buffer at pH 7.4 containing 300 mM imidazole. Purify complex over Superdex 200 (26/60) column. Elution Buffer: 50 mM Tris pH 7.4, 0.5 M NaCl, 1 mM EDTA, 10% glycerol, 10 mM β-ME. Dialyze peak fractions against previous Superdex 200 elution buffer containing 20 mM NaCl. Purify over Mono Q (5/50 GL) anion-exchange column. Elute in same buffer as above with linear NaCl gradient (20-600 mM NaCl). Flash-freeze fractions containing protein and store at −80° C.

Example 5

Purification of Cernunnos

Cernunnos purification was as follows: It was expressed in *E. Coli*. Purified over Ni-NTA beads. Fractions were run over a Superdex-200 gel filtration column. Peak fractions were then run over a HiTrap Heparin column and the purified proteins were stored at −80° C.

Example 6

DNA Joining Reaction

Mix 5 mM Ku, 5 mM DNA-PKcs, 0.5 mM XRCC4/Ligase IV, and 2.5 mM Cernunnos/XLF in End-Joining Buffer. Add protein mix to 10 ng/ul total DNA (800 bp fragments). Incubate at room temperature for 10 min. Add Mg-ATP to final concentrations of 5 mM $MgCl_2$ and 0.1 mM ATP. Total volume is 20 μl. Incubate at 37° C. for 30-45 min. Quench reaction with 2 ul 0.5 M EDTA. QIAQUICK purify DNA. PCR-amplify junction to measure joining efficiency. 1× End-Joining Buffer: 25 mM Tris pH 7.5, 75 mM NaCl, 72.5 mM KCl, 2 mM DTT, 50 μg/ml BSA, 0.025% Triton X-100, 5% Glycerol, 0.1 mM EDTA, 5% PEG MW>8000 kDa.

Example 7

The nonhomologous end-joining (NHEJ) pathway is conserved in eukaryotes from yeast to humans. Without requiring homologous DNA, NHEJ repairs DNA double-strand breaks produced by xenobiotic agents such as topoisomerase II inhibitors and ionizing radiation, or the cellular pathway for V(D)J recombination of the immunoglobulin genes. Even when the structure of the DNA ends prevents ligation, NHEJ processes the ends and repairs the breaks with high efficiency and minimal nucleotide loss. For ligatable ends such as the blunt signal ends created by V(D)J recombination, NHEJ suppresses processing and repairs the breaks directly. Thus, NHEJ optimizes the preservation of DNA sequence, but the mechanism is not understood.

Core proteins for NHEJ include Ku, DNA-dependent protein kinase catalytic subunit (DNA-PKcs) and XRCC4/Ligase IV (XL). Ku consists of two subunits, Ku70 and Ku86, binds with high affinity to DNA ends and recruits DNA-PKcs to the ends. DNA-PKcs brings the ends together into a synaptic complex and then undergoes activation of its kinase domain to facilitate later steps in the joining reaction. XL performs the final ligation step.

When the DNA ends cannot be ligated directly, NHEJ utilizes nuclease and polymerase activities to process the ends. The exo/endonuclease Artemis interacts with DNA-PKcs. Activation of the DNA-PKcs kinase facilitates Artemis endonuclease activity, which opens the hairpin ends created during V(D)J recombination. DNA polymerases mu and lambda interact with Ku and XL in vitro, and add nucleotides to the immunoglobulin light chain and heavy chain junctions, respectively, during V(D)J recombination.

Two groups recently identified a new NHEJ protein, designated Cernunnos or XRCC4-like factor (XLF); Buck et at. (2006) *Cell* 124, 287-99; Ahnesorg et al. (2006) *Cell* 124, 301-13. For simplicity, we will refer to the protein as Cernunnos for the remainder of this paper. Cernunnos was weakly homologous to XRCC4, but the amino acid sequence failed to suggest a potential function. Using purified proteins, we discovered that Cernunnos acting in concert with Ku stimulated XL to ligate one of the two strands from mismatched DNA ends. Furthermore, Cernunnos biased the choice of the ligated strand to optimize preservation of DNA sequence.

Results

Cernunnos promotes joining of mismatched and non-cohesive ends. We purified Ku, DNA-PKcs, XL, and Cernunnos to apparent homogeneity (FIG. 1A), and tested their ability to join cohesive 5' ends (EcoRI-EcoRI) or cohesive 3' ends (KpnI-KpnI). To measure joining efficiency, we used quantitative PCR, which amplified junctions produced from one pair of ends. The PCR primers eliminated signals from competing junctions, such as those produced from intramolecular ligation into circular monomers or intermolecular ligation of other ends. Ku, DNA-PKcs and XL joined EcoRI-EcoRI ends and KpnI-KpnI ends with efficiencies of 2.8% to 3.1% (FIG. 1B, rows 1 and 2). However, addition of Cernunnos had no effect on joining efficiency.

Next, we tested whether Cernunnos might affect the joining of non-cohesive DNA ends. Addition of Cernunnos to Ku, DNA-PKcs and XL stimulated joining of two blunt ends (EcoRV-EcoRV) by 6-fold (FIG. 1B, row 3). In the absence of Cernunnos, Ku, DNA-PKcs and XL joined blunt ends paired with either 5' or 3' overhangs with low and approximately equal efficiencies (rows 4-7). However, addition of Cernunnos stimulated joining 30 and 55-fold for the blunt-3' ends, EcoRV-KpnI and EcoRV-SacII, and 8 and 9-fold for the blunt-5' ends, EcoRV-EcoRI and EcoRV-BamHI. Thus, Cernunnos had a larger effect on blunt-3' ends than on blunt-5' ends.

Cernunnos also stimulated joining of ends with mismatched overhangs by 40 to 150-fold (rows 8-11). Ku, DNA-PKcs, XL and Cernunnos joined mismatched 5' overhangs (Acc65I-EcoRI, 0.0039%) with 23-fold lower efficiency than mismatched 3' overhangs (KpnI-SacI, 0.091%). However, Cernunnos facilitated more efficient joining when the 5' overhangs contained partially complementary sequences (BamHI-EcoRI, 0.25%).

Figure 6:
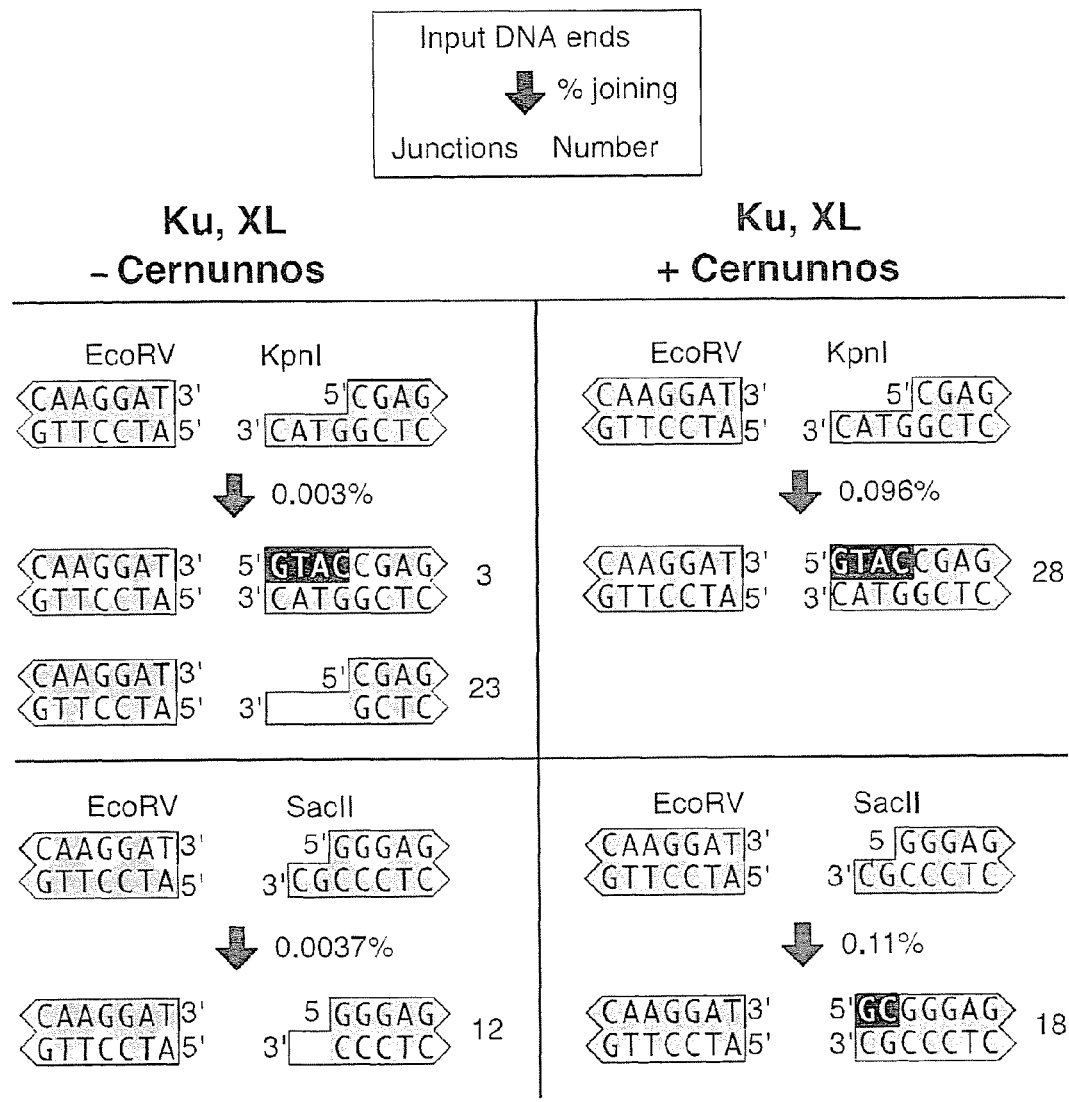
FIG. 6. Addition of Cernunnos to Ku and XL promotes the retention of 3' overhangs. We incubated DNA substrates with Ku and XL, with or without Cernunnos. The DNA substrates had mismatched blunt-3' ends with four nucleotide overhangs (EcoRV-KpnI) or blunt-3' ends with two nucleotide overhangs (EcoRVSacII). The junctions recovered from PCR amplification are depicted to show nucleotide addition (black background) and nucleotide deletion (white background).

In summary, Cernunnos exhibited a preference for 3' overhangs over 5' overhangs. This preference also occurred when we omitted DNA-PKcs from the joining reaction (FIG. 6). The effect of Cernunnos was specific, since Cernunnos had no effect on ligation of blunt ends to 3' overhangs by bacteriophage T4 DNA ligase (FIG. 7).

Cernunnos requires Ku to promote mismatched end joining by XL. We were particularly interested in the joining of mismatched 3' overhangs, because they are produced during V(D)J recombination in vivo, and because Cernunnos stimulated their joining by 40-fold in vitro (FIG. 1B, row 9). Interestingly, purified XL joined KpnI-SacI ends with low but detectable efficiency, but addition of Cernunnos failed to stimulate joining by XL alone (FIG. 2A). However, even a sub-stoichiometric concentration of Cernunnos (0.05 nM) stimulated joining by XL (0.5 nM) in the presence of Ku (5 nM) and DNA-PKcs (5 nM). A stoichiometric excess of Cernunnos (15 nM) stimulated joining 200-fold, up to a level of nearly 1%.

To determine which proteins were required for joining mismatched ends, we incubated the DNA with Ku, DNA-PKcs, XL and Cernunnos in different combinations (FIG.

2B). As single proteins, only XL produced detectable joining of the KpnI-SacI ends. Addition of Ku and DNA-PKcs to XL increased joining efficiency 12-fold. Starting from the reaction with all four protein preparations, we omitted each protein one at a time. Omission of DNA-PKcs reduced joining only 4-fold, but omission of Ku or Cernunnos reduced joining 150-fold or 40 fold, respectively. Note that omission of Cernunnos reduced joining 200-fold when the concentration of Cernunnos was 15 nM rather than 2.5 nM (FIG. 2A). Significantly, omission of XL eliminated joining activity completely. Thus, Ku, XL and Cernunnos were required for efficient joining of mismatched ends. These data suggested that Cernunnos and Ku stimulated a latent joining activity for mismatched ends contained in Ligase IV.

Figure 3:
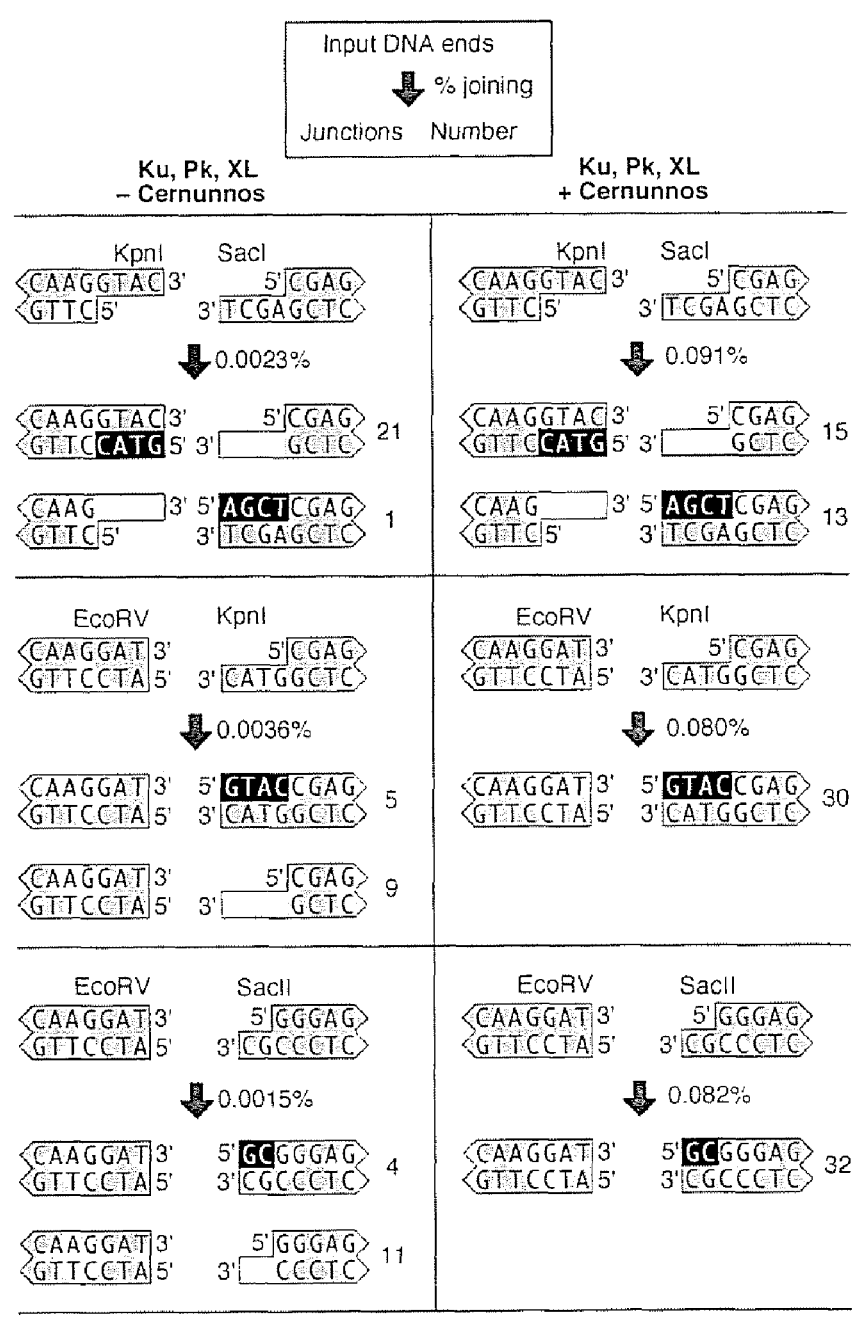

Cernunnos promotes preservation of 3' overhangs. To further characterize the joining of mismatched KpnI-SacI ends, we sequenced the junctions created by Ku, DNA-PKcs and XL, with or without addition of Cernunnos. Surprisingly, the sequence from one 3' overhang was retained in every junction, while the sequence of the other 3' overhang was lost (FIG. 3, upper panels). In the absence of Cernunnos, 21 of the 22 sequenced junctions retained the 3' KpnI overhang, while only 1 junction retained the SacI overhang. This preference occurred only in the absence of Cernunnos. In the presence of Cernunnos, the 3' overhangs were retained with equal probability.

Figure 8:
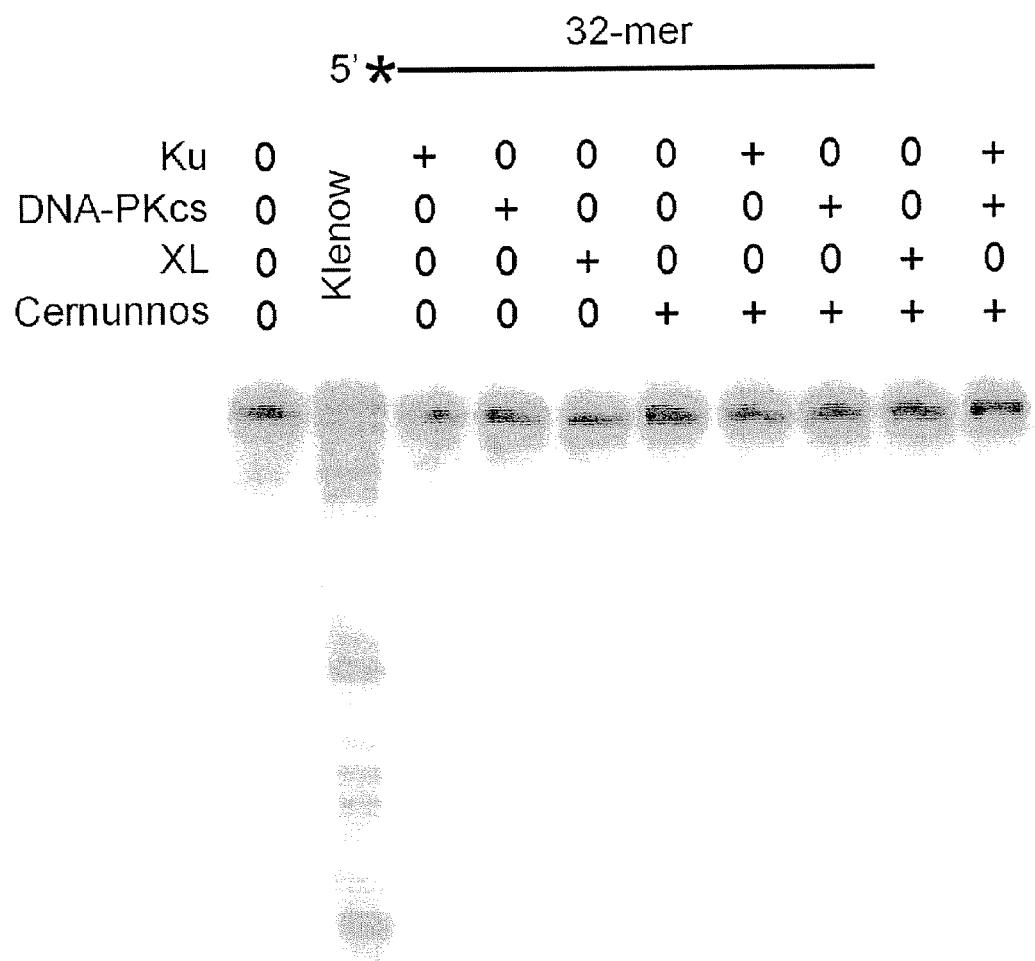
FIG. 8. Ku, DNA-PKcs, XL, and Cernunnos preparations lack detectable exonuclease activity. We labeled the 5' end of a 32-nt single-stranded DNA fragment with [g-32P]ATP and T4 polynucleotide kinase, and then incubated the DNA (0.5 mM) with different combinations of purified Ku (1.25 pmol), DNA-PKcs (1.25 pmol), XL (0.25 pmol), and Cernunnos (2.5 pmol) in a total volume of 10 ml at 37° C. for 30 min in 25 mM Tris (pH 8.0), 50 mM NaCl, 10 mM MgCl2, 1 mM DTT, and 50 ng/ml of BSA (lanes 3-10). As a positive control for nuclease activity, we incubated the DNA with Klenow fragment (0.2 unit), which contains a 3'-5' exonuclease activity, at room temperature for 45 min (lane 2). We stopped reactions by adding formamide gel loading buffer and heating at 95° C. for 2 min, resolved the DNA products on a 10% denaturing polyacrylamide gel, dried the gel, and analyzed the gel with Phosphorimager analysis (Molecular Dynamics) and ImageQuant quantitation software.

We also characterized the joining of blunt ends to 3' overhangs of four nucleotides (EcoRV-KpnI) or two nucleotides (EcoRV-SacII). In the absence of Cernunnos, most junctions (20 of 29) lost the 3' overhang, and only a minority (9 of 29) retained the 3' overhang (FIG. 3, middle and lower left panels). In the presence of Cernunnos, 62 of 62 sequenced junctions retained the 3' overhang (FIG. 3, right middle and right lower panels). Cernunnos exhibited the same effect when added to Ku and XL in the absence of DNA-PKcs (FIG. 8). Thus, the addition of Cernunnos promoted retention of sequences from the 3' overhangs.

Finally, we characterized the joining of blunt ends to 5' overhangs (FIG. 9). Cernunnos exhibited only a moderate effect in promoting retention of the 5' overhang for EcoRV-BamHI ends, and no effect on retention of the 5' overhang for EcoRV-EcoRI ends.

Ku, XL and Cernunnos ligate one of the two strands from mismatched DNA ends. In an effort to account for the retention or deletion of 3' overhangs, we examined our purified protein preparations for polymerase or nuclease activities. Polymerase activity was absent, since the joining reactions did not include dNTPs, and joining efficiency was unaffected by addition of dNTPs. Nuclease activity was also absent, since Cernunnos strongly stimulated joining of blunt-3' ends with retention of 3' overhanging sequences (FIG. 3 and FIG. 8). Furthermore, Cernunnos, Ku, XL and DNA-PKcs failed to degrade radiolabeled single-strand DNA substrates (FIG. 10), and did not delete any nucleotides in 112 junctions from pairs of blunt ends (EcoRV-EcoRV) and cohesive ends (EcoRI-EcoRI and KpnI-KpnI) (FIG. 11).

Figure 4:
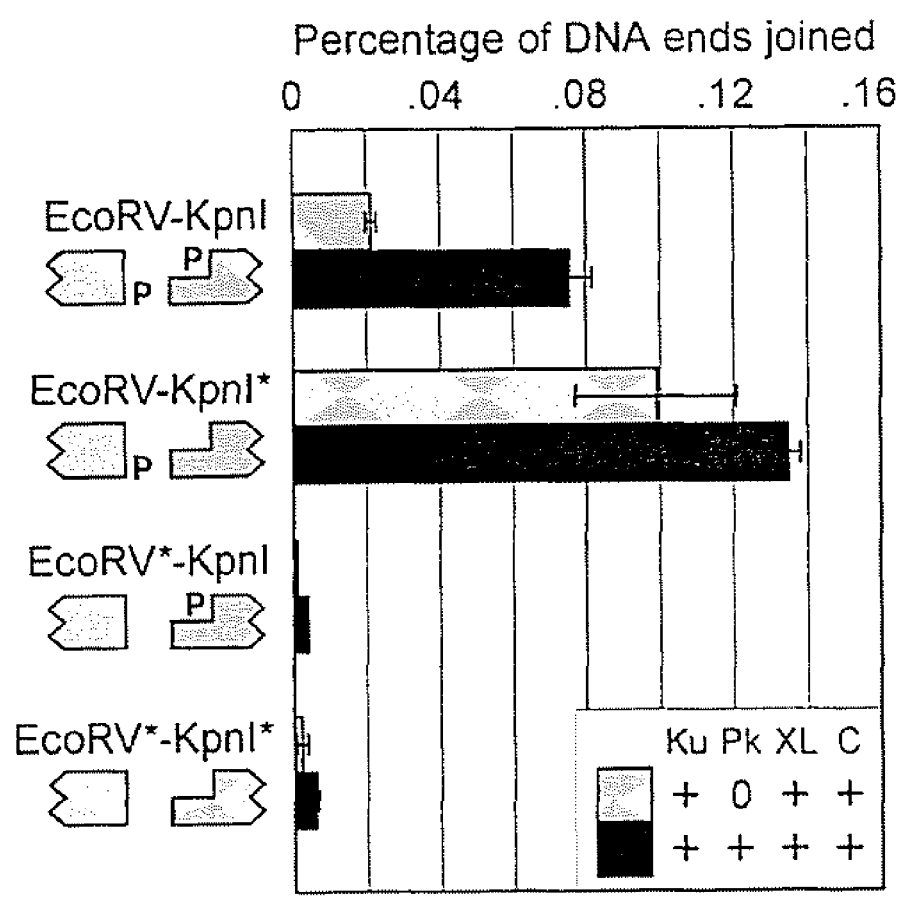
FIG. 4. Ku, XL and Cernunnos join mismatched ends using the 5' phosphate from only one end. To determine how Ku, XL and Cernunnos joined mismatched ends, we treated the EcoRV and KpnI substrates with DNA phosphatase (Antarctic phosphatase, NEB). EcoRV* and KpnI* denote dephosphorylated DNA molecules. We confirmed successful removal of the 5'-phosphates by incubating each DNA preparation with T4 ligase, and demonstrating loss of more than 90% of the ligation products by agarose gel electrophoresis. We incubated mismatched DNA substrates (EcoRV-KpnI, EcoRV-KpnI*, EcoRV*-KpnI or EcoRV*-KpnI*) with Ku, XL (1 nM) and Cernunnos (2 nM), with or without DNA-PKcs, amplified the junctions by quantitative PCR, and plotted joining efficiency on a linear scale.

Taken together, our data demonstrated that Cernunnos and Ku stimulated XL to ligate one of the two strands from mismatched DNA ends. Deletion or retention of 3' overhangs would depend on which strand was ligated. If Ligase IV catalyzes ligation of only one strand from mismatched ends, the 5' phosphate group of one DNA substrate should be dispensable for ligation. To test this, we removed 5' phosphates from the DNA substrates with 3' overhanging KpnI ends or blunt EcoRV ends, and incubated the DNA with Ku, XL and Cernunnos with or without DNA-PKcs (FIG. 4). When we removed the recessed 5' phosphate on the KpnI end, joining actually increased because of decreased competition from intramolecular circularization of the KpnI substrate. This demonstrated that the 5' phosphate on the KpnI end was dispensable for joining. By contrast, when we removed the 5' phosphate from the blunt EcoRV end, joining decreased to the levels observed when both DNA ends lacked 5' phosphates. Taken together with the junction sequences (FIG. 3), these data indicated that Cernunnos stimulated ligation of one strand from each end, joining the overhanging 3' hydroxyl on the KpnI end to the 5' phosphate on the blunt EcoRV end.

Figure 5:
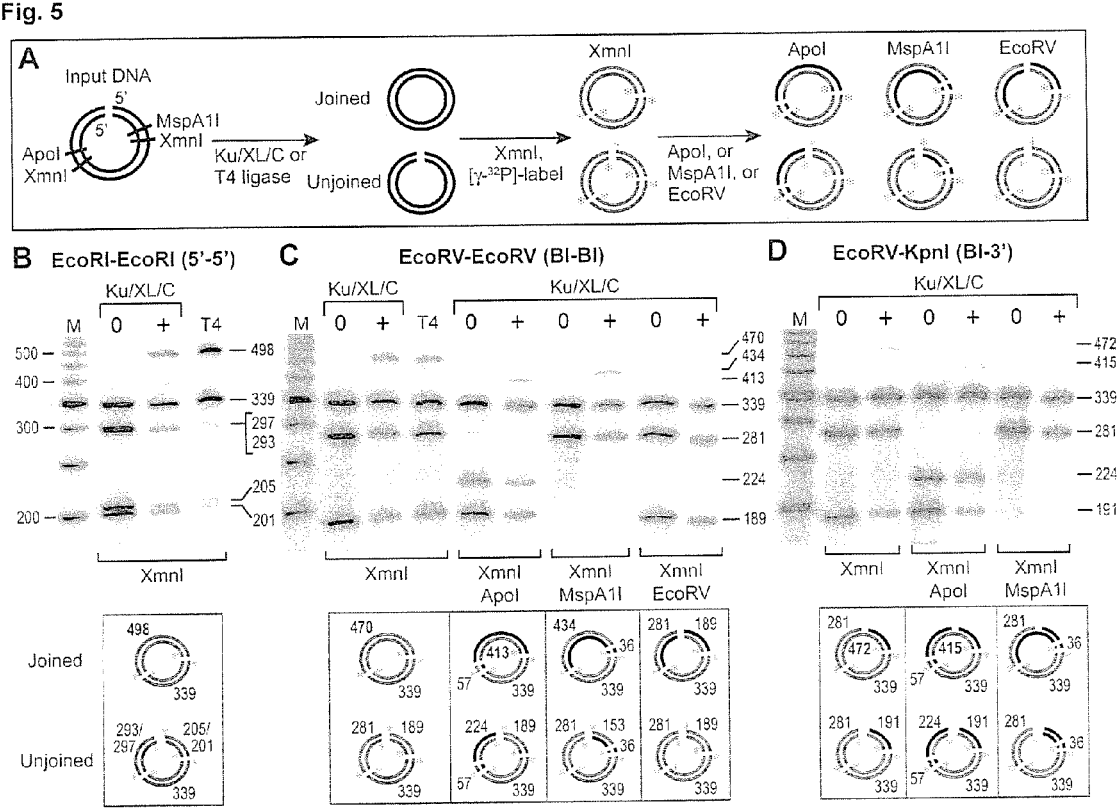
FIGS. 5A-D. Ku, XL and Cernunnos join mismatched ends by ligation of one strand. (A) Schematic of the gel-based assay for joining. We incubated Ku, XL and Cernunnos (Ku/XL/C) or T4 ligase (T4) with a linear DNA substrate containing EcoRI-EcoRI, EcoRV-EcoRV or EcoRV-KpnI ends, digested the DNA products with XmnI, and used T4 polynucleotide kinase to radiolabel the DNA. Concentrations of XL and Cernunnos were 1 nM and 5 nM, respectively. For EcoRV-EcoRV and EcoRV-KpnI ends, we performed a second digest with ApoI or MspA1I to remove radiolabel from one DNA strand. To confirm that ligation created a new phosphodiester bond, we digested the products of the EcoRV-EcoRV joining reaction with EcoRV. The figure depicts radiolabeled DNA strands in red with red asterisks at the 5' end, and unlabeled DNA strands in black. DNA products were resolved by denaturing gel electrophoresis. (B) Ku, XL and Cernunnos joined cohesive EcoRI-EcoRI ends. Ku, XL and Cernunnos (lane 3) and T4 ligase (lane 4) produced a higher molecular weight band of 498 nucleotides (nt). The molecular weight markers consisted of a radiolabeled 50 bp ladder (lane 1). Joining efficiencies for Ku/XL/C and T4 (calculated from the ratio of intensities in the 498 nt band to the 339 nt band) were 39% and 89%, respectively. Sizes of the ligated higher molecular weight bands in (B), (C) and (D) appear in blue typeface. (C) Ku, XL and Cernunnos joined blunt EcoRV-EcoRV ends. Ku, XL and Cernunnos (lane 3) and T4 ligase (lane 4) produced a higher molecular weight band of 470 nt, with joining efficiencies of 20% and 14%, respectively. ApoI digestion converted the 470 nt band to 413 nt and 57 nt bands, and converted the 281 nt band to 224 nt and 57 nt bands (lane 6). MspA1I digestion converted the 470 nt band to 434 nt and 36 nt bands, and the 189 nt band to 153 nt and 36 nt bands (lane 8). Intensities of the 413 nt and 434 nt bands were reduced to 50% of the 470 nt band because the second digestion removed the radiolabel from one strand. EcoRV digestion eliminated the 470 nt band (lane 10), demonstrating that the DNA junction contained new phosphodiester bonds. The 153 nt, 57 nt and 36 nt bands are not shown. (D) Ku, XL and Cernunnos joined only one strand from mismatched EcoRV-KpnI ends. Ku, XL and Cernunnos (lane 3) produced a higher molecular weight band of 472 nt, with a joining efficiency of 5%. ApoI digestion converted the 472 nt band to 415 nt and 57 nt bands, and the 281 nt band to 224 nt and 57 nt bands (lane 5). The intensities of the 472 nt and 415 nt bands were equivalent (lanes 3 and 5). MspA1I digestion converted the 472 nt band to a 36 nt band, and converted the 191 nt band to a 36 nt band (lane 7), demonstrating ligation of only one strand.

We wanted to obtain direct evidence for this mismatched end (MEnd) ligase activity without PCR amplification. Therefore, we designed a gel-based assay with radiolabeled DNA. To unambiguously identify the joined products and improve joining efficiency, we assayed intramolecular joining of linear DNA molecules. Each DNA molecule contained cohesive EcoRI-EcoRI ends, blunt EcoRV-EcoRV ends, or mismatched blunt-3' EcoRV-KpnI ends (FIG. 5).

We incubated the DNA with Ku, XL and Cernunnos. To detect the joined products by denaturing gel electrophoresis, we cleaved the DNA products with XmnI, and labeled the ends with [$\gamma$-$^{32}$P]ATP and T4 polynucleotide kinase (FIG. 5A). This procedure labeled the 5' ends of DNA strands terminating at XmnI, EcoRI, and EcoRV sites. We measured joining by appearance of a higher molecular weight DNA fragment of the appropriate size. To determine whether joining occurred for a specific strand, we removed the radiolabel on one strand or the other by cleaving the DNA with ApoI or MspA1I.

For the cohesive 5' overhanging EcoRI-EcoRI ends (FIG. 5B), Ku, XL and Cernunnos joined 39% of the input DNA. By contrast, T4 ligase joined 89% of the input DNA. For blunt EcoRV-EcoRV ends (FIG. 5C), Ku, XL and Cernunnos joined 20% and T4 ligase joined 14% of the input DNA. When we removed the radiolabel from one strand by cleaving the DNA with ApoI or MspA1I, 50% of the signal from the higher molecular weight DNA disappeared (FIG. 5C). Thus, the assay was able to discriminate the joining of one strand versus the other. The junction formed by joining of the blunt EcoRV ends was susceptible to cleavage by the phosphodiesterase activity of EcoRV, indicating that Cernunnos stimulated a ligation event that created a bona fide phosphodiester bond.

For blunt-3' EcoRV-KpnI ends, Ku, XL and Cernunnos joined 5% of the input DNA (FIG. 5D). This was higher than the result from quantitative PCR of the same DNA products, which detected ligation of 1.6% of the input DNA. When we removed the radiolabel from the strand containing the 3' overhang by MspA1I cleavage, 100% of the signal from the higher molecular weight DNA disappeared. By contrast, removal of the radiolabel from the other strand by ApoI reduced the size of the higher molecular weight fragment by 57 nucleotides without diminishing the signal. This result provided direct evidence for single-strand ligation of the hydroxyl group of the 3' overhang to the 5' phosphate of the blunt end. Remarkably, Ku, XL and Cernunnos ligated blunt-3' ends with an efficiency of 5%, even in the absence of DNA-PKcs.

We propose that Ku, XL and Cernunnos ligate the 3' overhanging hydroxyl group to the 5' phosphate of the opposing end. Thus, ligation creates a continuous single strand, which can serve as a template for DNA polymerase. Previously, we showed that human cell extracts recapitulated NHEJ as observed in vivo (Budman and Chu) (2005) *EMBO J.* 24, 849-60. Extracts join blunt-3' ends with high efficiency, utilizing polymerase activity to preserve the sequence from the 3' overhang. MEnd ligase activity explains this phenomenon.

We speculate that Cernunnos together with Ku and XRCC4 aligns mismatched ends to promote ligation by Ligase IV. It is shown herein that Cernunnos and Ku stimulated XL to join blunt ends and several types of mismatched ends that are non-complementary or partially complementary (FIG. 1). On the other hand, Cernunnos failed to stimulate joining of ends with cohesive 4 nucleotide overhangs. Thus, Cernunnos may be dispensable for cohesive end joining with 4 nucleotide overhangs, but may provide the necessary alignment for XL to join blunt ends, ends that are less cohesive, or ends with mismatched overhangs.

Ma et al. (2004) *Mol Cell* 16, 701-13. reported a single-strand ligase activity for XL alone. However, joining required alignment of the ends by at least 2 complementary base pairs, and occurred in the absence of Ku or Cernunnos. As shown herein, Cernunnos and Ku stimulated XL to ligate mismatched ends by more than 100-fold (FIG. 2B), even when the ends lacked complementary base pairing. Thus, Ku, XL and Cernunnos possess a novel ligase activity for mismatched ends.

In conclusion, the MEnd ligase activity from Ku, XL and Cernunnos preserves sequences by direct ligation of the 3' overhang to the 5' phosphate of the opposing end. MEnd ligase activity for mismatched ends has applications for recombinant DNA technology. For example, sheared genomic DNA and PCR-amplified DNA contain 3' overhangs generated by the shearing process or by the weak TdT activity of Taq polymerase, respectively. MEnd ligase can ligate such DNA molecules directly into a blunt-ended cloning vector.

Materials and Methods

Expression constructs and protein purification. We used PCR to amplify the human Cernunnos open reading frame (ORF) from a human cDNA clone (ATCC, MGC-32656), subcloned it into pET101/D-TOPO (Invitrogen), which added a His tag to the C-terminus of the protein, and expressed recombinant Cernunnos in bacteria. We purified Cernunnos from the bacterial lysate to apparent homogeneity on Ni-NTA beads (Qiagen) followed by Superdex-200 (26/60) and Hi-trap heparin columns (Amersham Pharmacia Biotech).

We purified XRCC4/Ligase IV as described above. Briefly, we infected Sf9 insect cells with baculoviruses containing XRCC4 and Ligase IV-His, lysed the cells, and purified the proteins on Ni-NTA beads (Qiagen) followed by Superdex-200 (26/60) and Mono Q (5/50 GL) columns (Amersham Pharmacia Biotech).

We purified Ku from lysate of Sf9 cells co-infected with baculoviruses containing Ku70-His and Ku86 by binding to Ni-NTA beads (Qiagen), and gel filtration on a Superose-12 (HR 10/30) column (Amersham Pharmacia Biotech).

We purified DNA-PKcs from HeLa cells, which were provided as a cell pellet by National Cell Culture Center. We prepared extracts with minor modifications of the protocol by Dvir et al. (1993) *J. Biol. Chem.* 268, 10440-10447 and purified DNA-PKcs using methods from Ding et al. (2003) *Mol Cell Biol* 23, 5836-48. Peak fractions containing Cernunnos, XRCC4/Ligase IV, Ku, and DNA-PKcs were flash-frozen and stored at −80° C.

Preparation of DNA substrates. We prepared DNA substrates for the PCR-based assay as previously described by Budman and Chu (2006) *Methods Enzymol* 408, 430-44, and prepared DNA substrates for the gel-based assay by PCR amplification of a 1 kb DNA fragment. Digestion of the PCR product with EcoRI or EcoRV, or double digestion with EcoRV and KpnI, released a DNA fragment with EcoRI-EcoRI, EcoRV-EcoRV, or EcoRV-KpnI ends, which was resolved by agarose gel electrophoresis and purified from the gel.

End-joining reactions. We performed end-joining reactions, purified the DNA products on a QIAquick column (Qiagen), measured joining efficiencies by quantitative PCR, and sequenced the DNA junctions.

For the gel-based assay, we performed end-joining reactions by incubating 0.4 pmol of the DNA substrate with no protein, or 2 pmol Ku, 0.4 pmol XL, and 2 pmol Cernunnos, or 1 unit of T4 DNA ligase (USB) in NHEJ buffer in a total volume of 200 μL. After incubation, we purified the DNA products on a QIAquick column (Qiagen), digested the DNA with XmnI at 37° C. for 1 hr, dephosphorylated the DNA with 1 unit Antarctic phosphatase (NEB) at 37° C. for 15 min, and then labeled the DNA with [γ-$^{32}$P]ATP and T4 polynucleotide kinase (NEB). We purified the DNA by phenol/chloroform extraction and ethanol-precipitation, digested the DNA further with ApoI, MspA1I, or EcoRV, resolved the products by electrophoresis in a TBE-urea 5% polyacrylamide gel (Bio-Rad), and quantified joining by PhosphorImager analysis (Molecular Dynamics).

Expression Constructs and Protein Purification. We used PCR to amplify the human Cernunnos ORF from a human cDNA clone (ATCC, MGC-32656) and subcloned it into pET101/D-TOPO (Invitrogen), which added a His tag to the C terminus of the protein. We verified the construct by DNA sequencing and expressed recombinant Cernunnos protein in the bacterial host Rosetta2(DE3)pLysS (EMD Biosciences).

To purify Cernunnos, we first induced expression by adding IPTG to 0.5 mM and grew cells for 3 h at 30° C., then extracted proteins in Buffer A (50 mM Na.PO$_4$, pH 8.0/2 M NaCl/10 mM imidazole/10 mM 2-βmercaptoethanol/1.5% Igepal CA-650/1 mM phenylmethylsulfonyl fluoride/2 mM benzamidine/EDTA-free protease inhibitor mixture tablet; Roche) and clarified the lysate by centrifugation at 35,000×g for 1 h. Lysate was loaded onto a Ni-NTA column (Qiagen), and bound proteins were eluted with 250 mM imidazole (100% Buffer A). We then pooled the fractions and subjected them to gel filtration on a Superdex-200 column in 1 M NaCl/20 mM Hepes, pH 8.0/10 mM 2-mercaptoethanol/1 mM EDTA/10% glycerol. We analyzed fractions by SDS/PAGE and Coomassie staining, pooled the fractions containing Cernunnos, loaded the pooled fractions onto a 1-ml Hi-Trap heparin column (Amersham Pharmacia Biotech), and applied a linear salt gradient of 150 to 1000 mM NaCl in Na.PO$_4$.

We purified XRCC4/Ligase IV by infectingSf9 cells with baculoviruses containing XRCC4 and Ligase IV-His (a gift from William Dynan, Medical College of Georgia, Augusta, Ga.), lysed the cells, and purified the proteins on a Ni-NTA column (Qiagen) followed by Superdex-200 (26/60) and Mono Q (5/50 GL) columns (Amersham Pharmacia Biotech).

We purified Ku70/86 from Sf9 cells coinfected with baculoviruses containing Ku70-His and Ku86 by lysing the cells in Buffer B (50 mM Na.PO$_4$, pH 8.0/500 mM NaCl/1.5% Igepal CA-650/10% glycerol/10 mM 2-mercaptoethanol/1 mM phenylmethylsulfonyl fluoride/2 mM benzamidine/EDTA-free protease inhibitor mixture tablet; Roche) and clarifying the extract with centrifugation. After binding proteins to Ni-NTA beads (Qiagen), we eluted Ku70/86 in Buffer B containing 300 mM imidazole and further purified the heterodimeric complex with a Superose-12 (HR 10/30) gel filtration column (Amersham Pharmacia Biotech) in 50 mM Na.PO$_4$, pH 7.4/300 mM NaCl/1 mM EDTA/10% glycerol/10 mM 2-mercaptoethanol. We purified DNA-PKcs from 20 liters of cultured HeLa cells, which were provided as a cell pellet by National Cell Culture Center.

We prepared nuclear extracts with minor modifications of the protocol by Dvir et al. In particular, we lysed cells by homogenization in hypotonic lysis buffer (10 mM KCl/10 mM Tris.HCl, pH 7.9/1 mM DTT/1 mM phenylmethylsulfonyl fluoride/2 mM benzamidine/EDTA-free protease inhibitor mixture tablet; Roche), collected cell nuclei by centrifugation at 3,300'g, and lysed the nuclei in buffer containing 50 mM Tris.HCl, pH 7.9/0.42 M KCl/5 mM MgCl2/20% glycerol/10% sucrose/2 mM DTT/1 mM phenylmethylsulfonyl fluoride/2 mM benzamidine/EDTA-free protease inhibitor mixture tablet. We collected nuclear proteins by centrifugation at 26,500×g followed by precipitation of the supernatant with 0.33 g/ml (NH$_4$)$_2$SO$_4$. The pellet was resuspended in 50 mM Tris.HCl, pH 7.9/0.1 M KCl/12.5 mM MgCl$_2$/1 mM EDTA/20% glycerol/1 mM DTT and dialyzed into the same buffer. We purified DNA-PKcs by loading nuclear extract onto a column of NHS-activated HiTrap resin (Invitrogen) conjugated to a Ku86 C-terminal peptide, and eluting bound protein in 25 mM Hepes-KOH, pH 7.5/0.

What is claimed is:

1. A method of efficiently catalyzing direct ligation of noncompatible DNA ends in vitro, the method comprising:
   contacting in a reaction mix a purified mismatched end DNA ligase complex comprising the polypeptides Ku, Cernunnos, and XRCC4/Ligase4, and DNA comprising non-compatible ends, in the presence of ATP for a period of time sufficient to permit direct ligation and preservation of DNA sequence, wherein the efficiency of ligation is at least 10% of a comparable reaction with DNA comprising compatible ends.

2. The method according to claim 1, wherein said purified mismatched end DNA ligase complex further comprises DNA-PK.

3. The method according to claim 1, wherein at least one of said noncompatible ends has a 3' overhangs.

4. The method according to claim 1, wherein at least one of said ends is a blunt end.

5. The method according to claim 1, wherein at least one of said DNA comprising non-compatible ends is a single stranded DNA.

6. A method of efficiently catalyzing direct ligation of noncompatible DNA ends in vitro, the method comprising:
   contacting in a reaction mix a mismatched end DNA ligase complex consisting of substantially pure Ku, Cernunnos, XRCC4/Ligase4 and DNA-PK, and DNA comprising non-compatible ends, in the presence of ATP for a period of time sufficient to permit direct ligation and preservation of DNA sequence, wherein the efficiency of ligation is at least 10% of a comparable reaction with DNA comprising compatible ends.

7. The method according to claim 6, wherein said DNA ligase complex consists of eukaryotic polypeptides.

8. The method according to claim 7, wherein said eukaryotic polypeptides are mammalian polypeptides.

9. A method of catalyzing direct ligation of DNA ends, the method comprising:
   contacting in a reaction mix a purified mismatched end DNA ligase complex consisting of substantially pure Ku, Cernunnos, XRCC4/Ligase4 and DNA-PK, and DNA, in the presence of ATP for a period of time sufficient to permit direct ligation and preservation of DNA sequence.

10. The method according to claim 9, wherein said DNA ligase complex consists of eukaryotic polypeptides.

11. The method according to claim 10, wherein said eukaryotic polypeptides are mammalian polypeptides.

\* \* \* \* \*

SEQUENCE LISTING

<160> NUMBER OF SEQ ID NOS: 1

<210> SEQ ID NO 1
<211> LENGTH: 17
<212> TYPE: PRT
<213> ORGANISM: Artificial Sequence
<220> FEATURE:
<223> OTHER INFORMATION: Ku80C-derived synthetic peptide

<400> SEQUENCE: 1

Lys Gly Ser Gly Glu Glu Gly Gly Asp Val Asp Asp Leu Leu Asp Met
 1               5                  10                  15

Ile